US012653712B2

(12) United States Patent
Axelrad et al.

(10) Patent No.: US 12,653,712 B2
(45) Date of Patent: Jun. 16, 2026

(54) NASAL DILATOR SYSTEM

(71) Applicant: Breathewave Technologies Inc., Edgewater, NJ (US)

(72) Inventors: David J. Axelrad, Closter, NJ (US); Michael A. Linn, Ridgewood, NJ (US); Geoffrey P. Waite, Campton, NH (US); Christopher A. Beaudreau, Parker, CO (US)

(73) Assignee: Breathewave Technologies Inc., Edgewater, NJ (US)

( * ) Notice: Subject to any disclaimer, the term of this patent is extended or adjusted under 35 U.S.C. 154(b) by 43 days.

(21) Appl. No.: 18/952,352

(22) Filed: Nov. 19, 2024

(65) Prior Publication Data

US 2025/0161090 A1 May 22, 2025

Related U.S. Application Data

(60) Provisional application No. 63/656,450, filed on Jun. 5, 2024, provisional application No. 63/601,003, filed on Nov. 20, 2023.

(51) Int. Cl.
A61F 5/08 (2006.01)
(52) U.S. Cl.
CPC ..................................... A61F 5/08 (2013.01)
(58) Field of Classification Search
CPC ... A61F 5/08; A61F 5/56; A61F 2/186; A62B 23/06
See application file for complete search history.

(56) References Cited

U.S. PATENT DOCUMENTS

| | | | |
|---|---|---|---|
| 5,895,409 A | 4/1999 | Mehdizadeh |
| D737,965 S | 9/2015 | Bende |
| D952,845 S | 5/2022 | Herbst |
| 2017/0273626 A1 | 9/2017 | MacDonald |
| 2017/0281918 A1 | 10/2017 | Gross |
| 2020/0069321 A1 | 3/2020 | Zhao |
| 2020/0206547 A1 | 7/2020 | Hellman et al. |

(Continued)

FOREIGN PATENT DOCUMENTS

| | | |
|---|---|---|
| CN | 216702736 U | 6/2022 |
| KR | 10-2022-0080242 A | 6/2022 |

(Continued)

OTHER PUBLICATIONS

Gelardi et al., "Internal and external nasal dilatator in patients who snore: a comparison in clinical practice", Acta Biomed, 2019;90(Suppl 2):10-14.

(Continued)

*Primary Examiner* — Ashley L Fishback
(74) *Attorney, Agent, or Firm* — Morse, Barnes-Brown & Pendleton P.C.; Sean D. Detweiler, Esq.

(57) ABSTRACT

A nasal dilation system has at least two sets of nasal dilators. Each set includes one or more nasal inserts having a mesh wall comprised of interconnected struts and openings. The mesh wall forms a cannula. The inserts are designed to engage with the inner surface of nasal passages. The pattern of struts and openings of a first set differs from a second set, resulting in different impact patterns on the inner surface of nasal passages, reducing repeated impact of the same inner surface portion across multiple sets of nasal dilators.

26 Claims, 8 Drawing Sheets

(56)                   References Cited

U.S. PATENT DOCUMENTS

| | | |
|---|---|---|
| 2021/0085509 A1 | 3/2021 | Magness |
| 2022/0117726 A1 | 4/2022 | Rosenthal et al. |
| 2023/0046852 A1 | 2/2023 | Abbate |
| 2023/0320888 A1 | 10/2023 | Pepper et al. |
| 2025/0375598 A1 | 12/2025 | Axelrad et al. |

FOREIGN PATENT DOCUMENTS

| | | | |
|---|---|---|---|
| WO | WO-2021063729 A1 * | 4/2021 | ........ A61M 16/0688 |
| WO | 2025/111253 A1 | 5/2025 | |
| WO | 2025/255263 A1 | 12/2025 | |

OTHER PUBLICATIONS

International Search Report for International Application No. PCT/US2025/032322 mailed Aug. 25, 2025.
International Search Report for International Application No. PCT/US2024/056497 mailed Feb. 6, 2025.
"Max-Air Nose Cones—Nasal Breathing Relief for Sleep and Snoring—Soft Comfort Nasal Device," retrieved from the internet, https://www.maxairnosecones.com/max-air-nose-cones/ 1/9, retrieved on Mar. 7, 2025.
"Snooze® Nostril Expanders—SQuiP Nasaline ," retrieved from the Internet <https://www.squipusa.com/product/snooze-nostril-expanders/,> retrieved on Mar. 7, 2025.
WoodyKnows Super-Support Nasal Dilators|Sleep Sports Breathing Aid|Soft Comfortable Nose Vents|Improve Breathe Airflow|Snoring Congestion Relief, retrieved from the Internet, <https://woodyknows.com/products/invisible-nasal-strips-snoring-snore-solution,> retrieved on Mar. 7, 2025.

* cited by examiner

102G

112G

114G

102H

112H

114H

102I

112I

114I

NASAL DILATOR SYSTEM

CROSS-REFERENCE TO RELATED APPLICATION(S)

This application claims priority to, and the benefit of, U.S. Provisional Application No. 63/601,003, filed Nov. 20, 2023, and claims priority to, and the benefit of, U.S. Provisional Application No. 63/656,450, filed Jun. 5, 2024, for all subject matter contained in said applications. The disclosures of said provisional applications are hereby incorporated by reference in their entirety.

FIELD OF THE INVENTION

The present invention relates to nasal dilators suitable for increasing airflow. In particular, the present invention relates to a nasal dilation system comprising multiple sets of nasal dilators, each with a different pattern of interconnected struts and openings, resulting in different impact patterns upon an inner surface of nasal passages of a user thereby reducing the repeated impact of a same inner surface portion across multiple uses of one or more nasal dilators.

BACKGROUND

Constriction of the nasal valve can be continuous, e.g., in someone with a collapsed or narrowed nasal valve (common after trauma and in old age, but also congenitally) or rhythmic, caused by the soft tissue of the nasal valve being "sucked in" by the venturi effect of breathing in. Such constrictions can cause i) snoring and/or sleep disturbance, including sleep apnea, and ii) awake and athletic performance hindrance due to insufficient airflow. Within the body of the nose, the soft tissue and cartilage of the lateral nasal wall is mainly responsible for the limitation of nasal airflow, although constriction by the middle turbinate can also create a significant limitation. Injured or older patients can experience softer nasal cartilage, which can lead to further weakening of the nasal structure with a tendency for collapse at the lateral nasal wall. Traditional methods for increasing airflow through obstructed nasal passages often involve the use of nasal dilators, which may be either external or internal.

However, the known technology, devices, systems, methodologies, etc. experiences some shortcomings. External nasal dilators, often referred to as nasal strips, rely on adhesive to attach to the outside user's nose and pull open the nostrils which can lose adhesion as the user sweats, or moves during sleep and can cause skin irritation. Internal nasal dilators are inserted into the nostril to push open the nostrils. These can become uncomfortable and unhealthy to use over time as the continuous, repeated impact on the internal surface of the nostril by the outer surface of the dilator can cause comfort and health issues such as chaffing, follicle infection, in-growing nasal hairs, etc.

SUMMARY

There is a need for a way to treat nasal valve narrowness and collapse that does not suffer from these shortcomings. The present invention is directed toward further solutions to address this need, in addition to having other desirable characteristics.

In accordance with embodiments of the present invention, a nasal dilation system is provided, having at least two sets of nasal dilators. Each set includes a first nasal insert and a second nasal insert. The first and second nasal inserts each have a mesh wall comprised of a plurality of interconnected struts and openings. The mesh wall forms a cannula extending between a base opening and a top opening. The first and second nasal inserts are sized, dimensioned, and configured in such a way as to be insertable to engage an outer surface of the mesh wall with an inner surface of nasal passages of a user, using a different insert of the set of inserts for each nasal passage. The pattern of the plurality of interconnected struts and openings of a first set of the at least two sets of nasal dilators differs from a pattern of the plurality of interconnected struts and openings of a second set of the at least two sets of nasal dilators and cycling between the first set and the second set results in different impact patterns of the mesh walls upon the inner surface of nasal passages of a user thereby reducing repeated impact of a same inner surface portion across multiple sets of nasal dilators.

In accordance with aspects of the present invention, the at least two sets of nasal dilators comprise three sets of nasal dilators. In other aspects, the at least two sets of nasal dilators comprise seven sets of nasal dilators.

In accordance with aspects of the present invention, the pattern of the plurality of interconnected struts and openings of the first nasal insert of a set instance of the at least two sets of nasal dilators differs from a pattern of the plurality of interconnected struts and openings of the second nasal insert of the set instance of the at least two sets of nasal dilators.

In accordance with aspects of the present invention, a cross-sectional area of each of the first and second inserts is substantially circular, ellipsoid, or rounded shape. In other aspects, a cross-sectional area of each of the first and second inserts varies along a length of the cannula. In still other aspects, a base opening cross-sectional area is greater than a top opening cross-sectional area.

In accordance with aspects of the present invention, the plurality of interconnected struts form irregular shaped openings therebetween. In other aspects, the plurality of interconnected struts and openings forms a non-uniform pattern.

In accordance with aspects of the present invention, the at least two sets of nasal dilators are formed of a pliant material. In some such aspects, the at least two sets of nasal dilators are formed of one or more of metal, plastic, polymer, and rubber.

In accordance with aspects of the present invention, the first and second nasal inserts are comprised of a biocompatible material.

In accordance with aspects of the present invention, the top opening is sized, dimensioned, and configured to maintain the first and second nasal inserts in place within the nasal passages via a friction fit. In other aspects, the base opening is sized, dimensioned, and configured to maintain the first and second nasal inserts in place within the nasal passages via a friction fit.

In accordance with aspects of the present invention, varying effects produced by the first and second nasal inserts upon an internal lining of nasal passages of the user comprises increased airflow through the nasal passages.

In accordance with aspects of the present invention, the at least two sets of nasal dilators further comprise identifiers to distinguish each set from another. In some such aspects, the identifiers comprise one or more of symbols, colors, and shapes.

In accordance with aspects of the present invention, the system further includes a storage case sized, dimensioned, and configured for storing the at least two sets of nasal dilators when not in use, the storage case optionally comprising identifiers formed of symbols, colors, and/or shapes.

In accordance with aspects of the present invention, the at least two sets of nasal dilators are disposable after a single use. In other aspects, the at least two sets of nasal dilators are reusable and can be cleaned or sterilized for repeated use.

In accordance with aspects of the present invention, the at least two sets of nasal dilators are provided in a variety of shapes to accommodate different shapes of nasal passages.

In accordance with aspects of the present invention, the system further includes a connector connecting the first inserts to the second insert proximal the base openings of each insert. In some such aspects, the connector is sized, shaped, and configured to apply a force on the first and second inserts pushing the first and second inserts together. In other such aspects, the connector is sized, shaped, and configured to apply a force on the first and second inserts pushing the first and second inserts apart.

In accordance with aspects of the present invention, the pattern of the plurality of interconnected struts and openings is generated via a randomizing process such as to be unique, at least across a very large number of variants.

In accordance with embodiments of the present invention, a nasal dilation system is provided, comprising at least two sets of nasal dilators. Each set includes at least one nasal insert having a mesh wall comprised of interconnected struts and openings, forming a cannula. The inserts are designed to engage with the inner surface of a user's nasal passages, with a different insert used for each passage. The pattern of struts and openings differs between sets of dilators, resulting in different impact patterns on the inner surface of the nasal passages, reducing repeated impact on the same inner surface portion across multiple sets of dilators.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
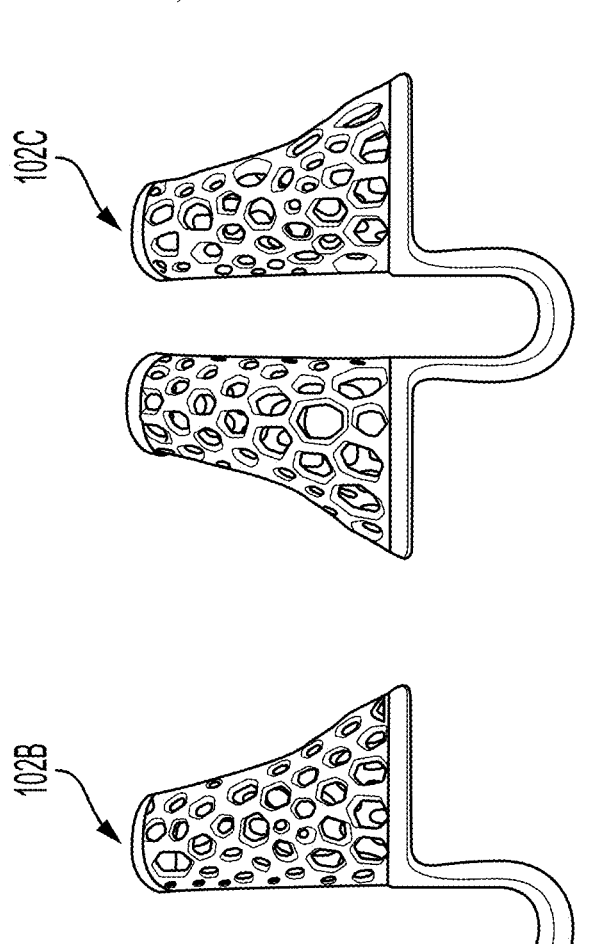
FIG. 1 is an example nasal dilator system in accordance with embodiments of the present invention.
Figure 1:
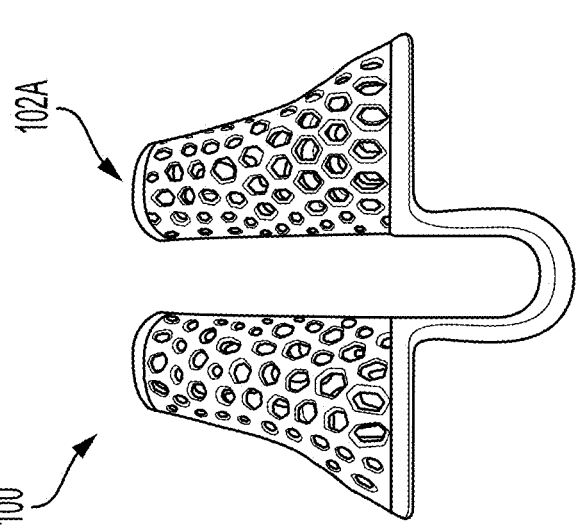

An illustrative embodiment of the present invention relates to a nasal dilation system comprising at least two sets of nasal dilators. Each dilator set includes one or more nasal inserts having a mesh wall comprised of interconnected struts and openings. The mesh wall forms a cannula. The inserts are designed to engage with the inner surface of nasal passages. The pattern of struts and openings of a first set differs from a second set, resulting in different impact patterns on the inner surface of nasal passages, reducing repeated impact of the same inner surface portion across multiple sets of nasal dilators.

FIG. 1 through FIG. 8 wherein like parts are designated by like reference numerals throughout, illustrate an example embodiment or embodiments of a nasal dilator system, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

The present disclosure relates to a nasal dilation system 100. In an example embodiment of FIG. 1, the system comprises at least two sets of nasal dilators 102 depicted as a first set of nasal dilators 102A, a second set of nasal dilators 102B, and a third set of nasal dilators 102C. Here, in the figures, individual sets of dilators 102 are further delineated with a letter A, B, and C. However, it should be understood that the sub-designations "A", "B" and "C" are merely provided to identify separate instances of a set of nasal dilators 102 of the nasal dilator system 100 and when discussing the generic part, the sub-designation may not be used.

Figure 2:
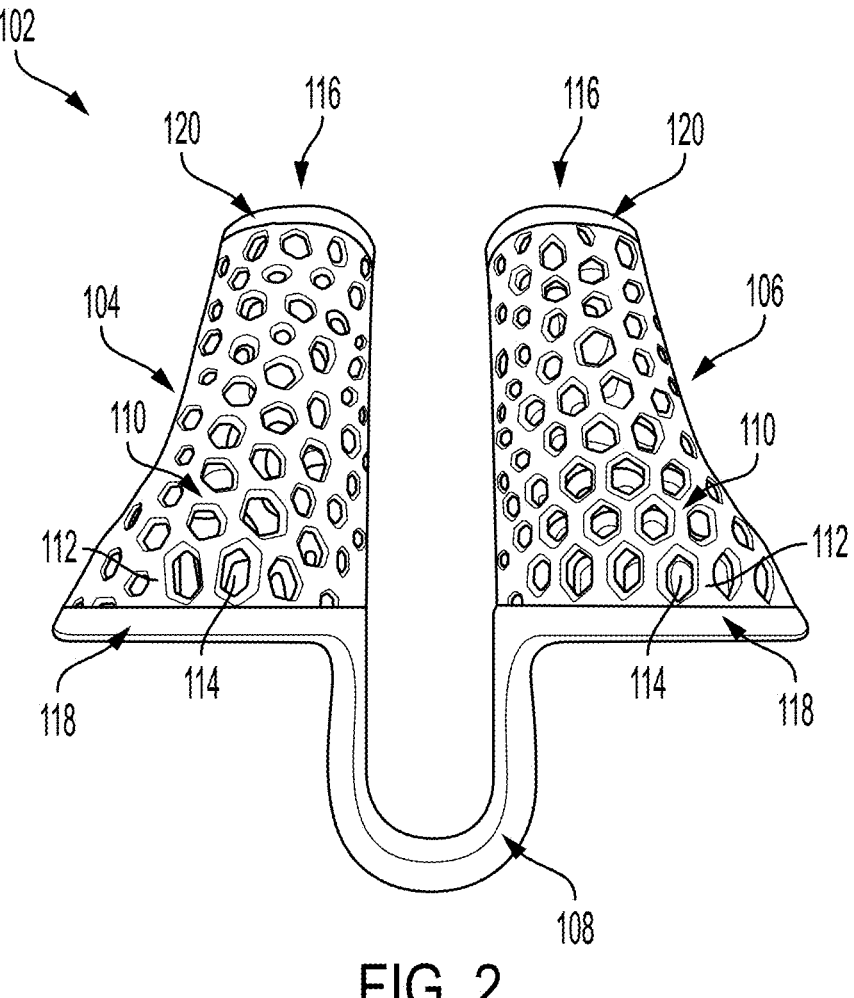
FIG. 2 is a single set of nasal dilators of the dilator system in accordance with embodiments of the present invention.
Figure 3:
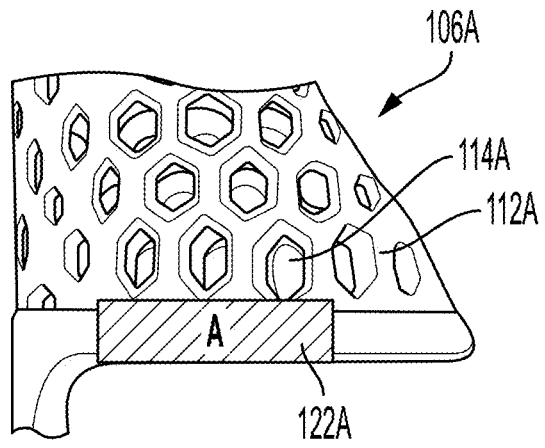
FIG. 3 is a close-up view of portions of the sets of nasal dilators of the system showing identifiers in accordance with embodiments of the present invention.
Figure 3:
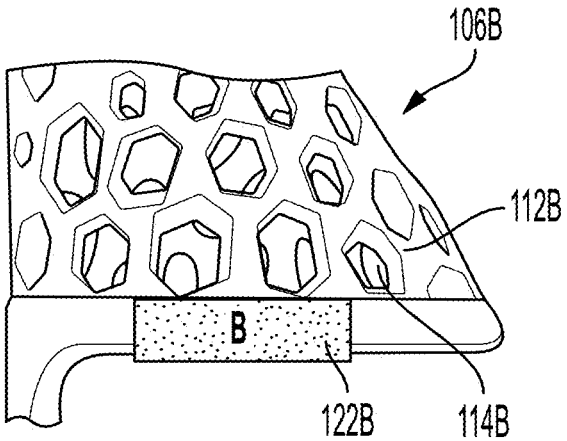
Figure 3:
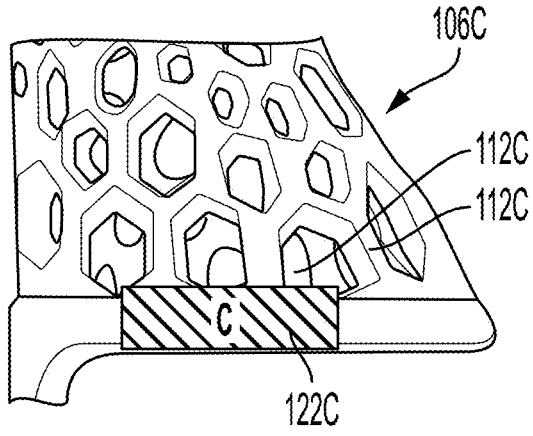

FIG. 2 shows a single set of nasal dilators 102. Here, the set of nasal dilators 102 includes a first nasal insert 104 and a second nasal insert 106. The first and second nasal inserts 104, 106 each have a mesh wall 110 comprised of a plurality of interconnected struts 112 and openings 114. The mesh wall 110 forms a cannula 116 extending between a base opening 118 and a top opening 120. In this embodiment, the base opening 118 cross-sectional area is greater than the top opening 120 cross-sectional area. In other embodiments, the base opening 118 cross-sectional area can be smaller or the same size as the top opening 120 cross-sectional area. In this embodiment, there is also a connector 108 that connects the first insert 104 to the second insert 106 proximal the base openings 118 of each insert 104, 106.

The first nasal insert 104 and second nasal insert 106 are sized, dimensioned, and configured in such a way as to be insertable to engage an outer surface of the mesh wall 110 with an inner surface of the nasal passages of a user. A different insert 104, 106 of the set of nasal dilators 102 is used for each nasal passage. In certain embodiments, varying effects produced by the first 104 and second 106 nasal inserts upon an internal lining of nasal passages of the user comprise increased airflow resulting from the set of nasal dilators 102 applying force against the nasal passages of a user, thereby maintaining an open breath way or channel for improved airflow. In some embodiments, a cross-sectional area of each of the first 104 and second 106 inserts of set 102, is substantially circular, ellipsoid, or other rounded shape. In some such embodiments, a cross-sectional area of each of the first 104 and second inserts 106 varies along a length of the cannula 116, as shown in the example presented here wherein the shape of the inserts 104, 106 is generally conical. However, it should be understood that the cross-sectional area could have any number of shapes and in some embodiments, the shape of the cross-sectional area could change along the length of the cannula 116. Other shapes and configurations will be apparent to one skilled in the art given the benefit of this disclosure.

While the examples presented here involve three sets of nasal dilators 102A, 102B, 102C, the present invention can be implemented with as few as two sets and can include any number of sets. In some such embodiments, there are seven sets of nasal dilators, enabling the use of a separate pair for each day of the week. In other embodiments, the at least two sets of nasal dilators 102 of the system 100 are provided in a variety of shapes and or sizes to accommodate different shapes of nasal passages. For example, the nasal dilator system 100 can be provided in different sizes such as small, medium, or large. Other shapes and configurations will be apparent to one skilled in the art given the benefit of this disclosure.

In the system, as shown in FIG. 1, each of the set of nasal dilators 102A, 102B, and 102C of nasal dilators is structurally different. Thus, the pattern of the plurality of interconnected struts 112 and openings 114 of the first set of nasal dilators 102A differs from a pattern of the plurality of interconnected struts and openings of the second set of nasal dilators 102B, which differs from a pattern of the plurality of interconnected struts and openings of the third set of nasal dilators 102C. Cycling between the first set of nasal dilators 102A and the second set of nasal dilators 102B (and in the example of FIG. 1, the third set of nasal dilators 102C) results in different impact patterns of the mesh walls upon an inner surface of nasal passages of a user. This reduces repeated impact of a same inner surface portion across multiple sets of nasal dilators 102 because, with the struts in different patterns, angles, and locations, they impact different portions of the inner surface of the nasal passages of the user.

The pattern of the interconnected struts 112 and openings 114 can involve any number of patterns or configurations. In certain embodiments, the plurality of interconnected struts 112 form irregular shaped openings 114 therebetween. In some embodiments, the plurality of interconnected 112 struts and openings 114 forms a non-uniform pattern across the set of nasal dilators 102. In certain embodiments, the pattern of the plurality of interconnected struts 112 and openings 114 is generated via a randomizing process such as to be unique, at least across a very large number of variants.

In some embodiments, the top opening 120 is sized, dimensioned, and configured to maintain the first 104 and second 106 nasal inserts in place within the nasal passages via a friction fit. In some embodiments, the base opening is sized, dimensioned, and configured to maintain the first and second nasal inserts in place within the nasal passages via a friction fit. Other patterns or configurations will be apparent to one skilled in the art given the benefit of this disclosure.

In certain embodiments, the at least two sets of nasal dilators 102 are formed of one or more of metal, plastic, polymer, and rubber. In certain embodiments, the at least two sets of nasal dilators 102 are formed of a pliant material. In some certain embodiments, the first 104 and second 106 nasal inserts are comprised of a biocompatible material, such as for example, silicone, polyurethane, polyethylene terephthalate (PET), and polylactic acid (PLA). Those of ordinary skill in the art will appreciate that other biocompatible materials can be utilized in accordance with the requirements and teachings of the present disclosure.

In some embodiments, the at least two sets of nasal dilators 102 further comprise identifiers 122 to distinguish each set from another. In some such embodiments, the identifiers 122 comprise one or more of symbols, colors, shapes, and electronically readable tags such as RFID, NFC, or a barcode. An example of this can be seen in FIG. 3. Here a close-up view of a section of the second inserts 106A, 106B, 106C of the sets of nasal dilators 102A, 102B, and 102C is shown having the identifiers 122A, 122B, 122C. In this case, a color and letter designation, serve as the identifiers. The variance in the pattern of the plurality of interconnected struts 112A, 112B, 112C and openings 114A, 114B, 114C between the sets of nasal dilators 102A, 102B, and 102C can also be seen in more detail in this figure.

Figure 4:
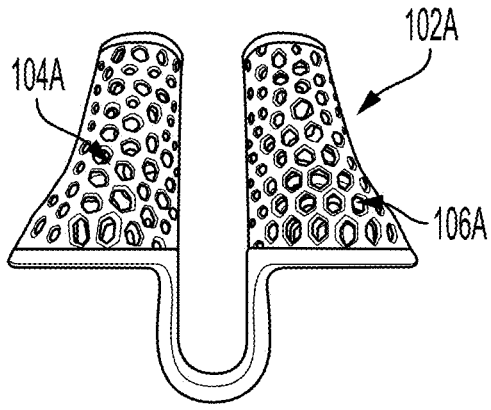
FIG. 4 is an example of a nasal dilator system where the sets of nasal dilators are color-coded in accordance with embodiments of the present invention.
Figure 4:
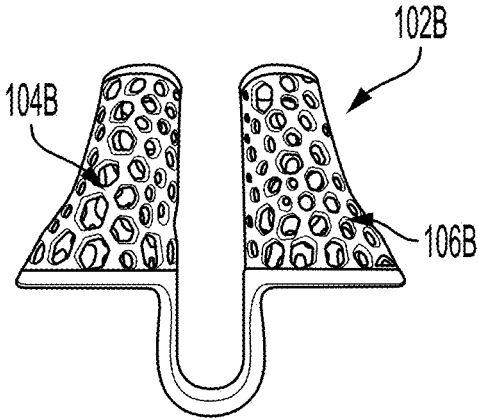
Figure 4:
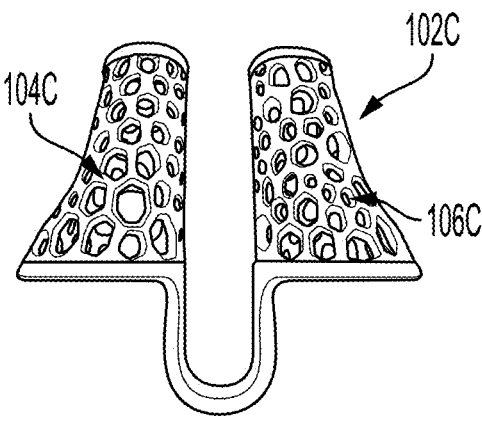
Figure 5:
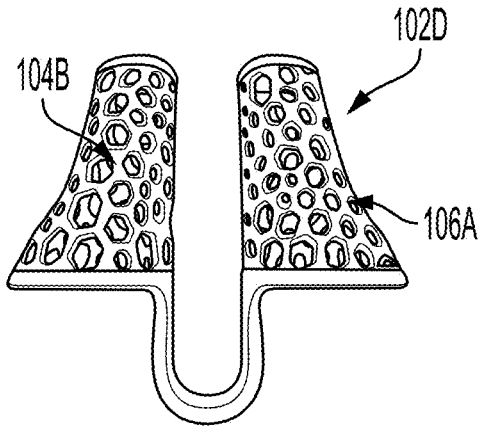
FIG. 5 is an example of a nasal dilator system wherein each insert of each set of nasal dilators has a different pattern in accordance with embodiments of the present invention.
Figure 5:
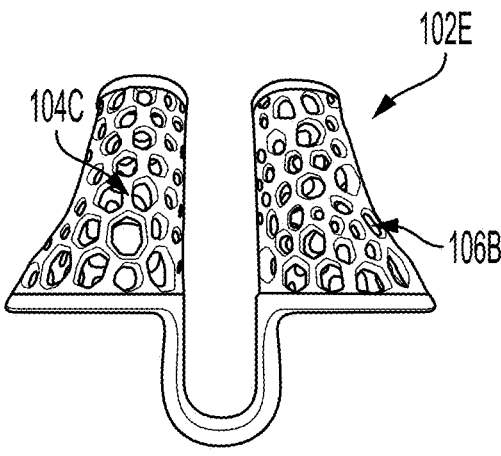
Figure 5:
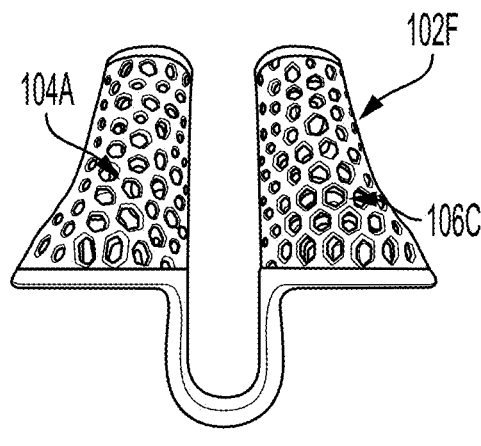

In the example of FIG. 4, the individual sets of nasal dilators 102A, 102B, and 102C are identified and otherwise delineated by the coloration of the entire set of nasal dilators 102.

Figure 6:
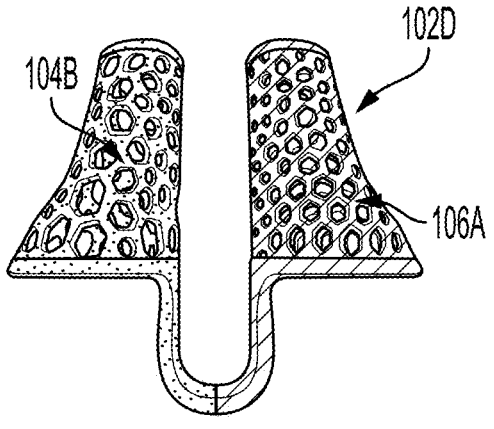
FIG. 6 is an example of the nasal dilator system of FIG. 5, wherein the inserts are color-coded as in FIG. 4.
Figure 6:
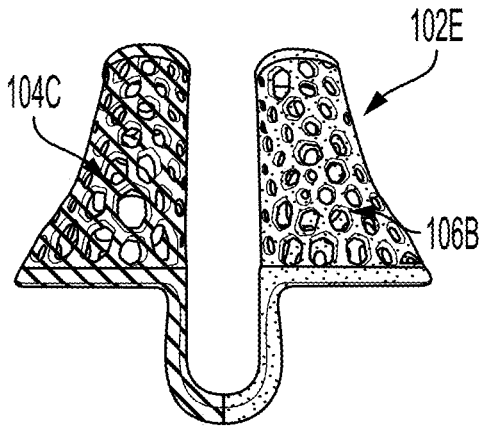
Figure 6:
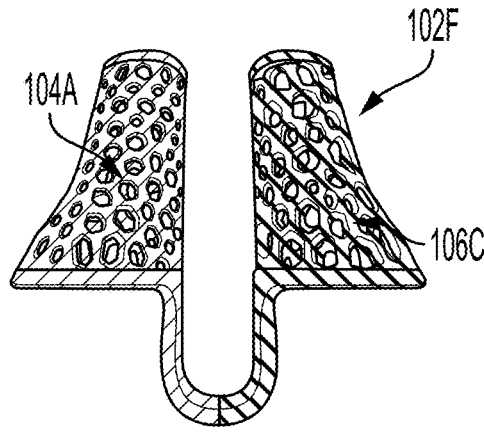
Figure 7:
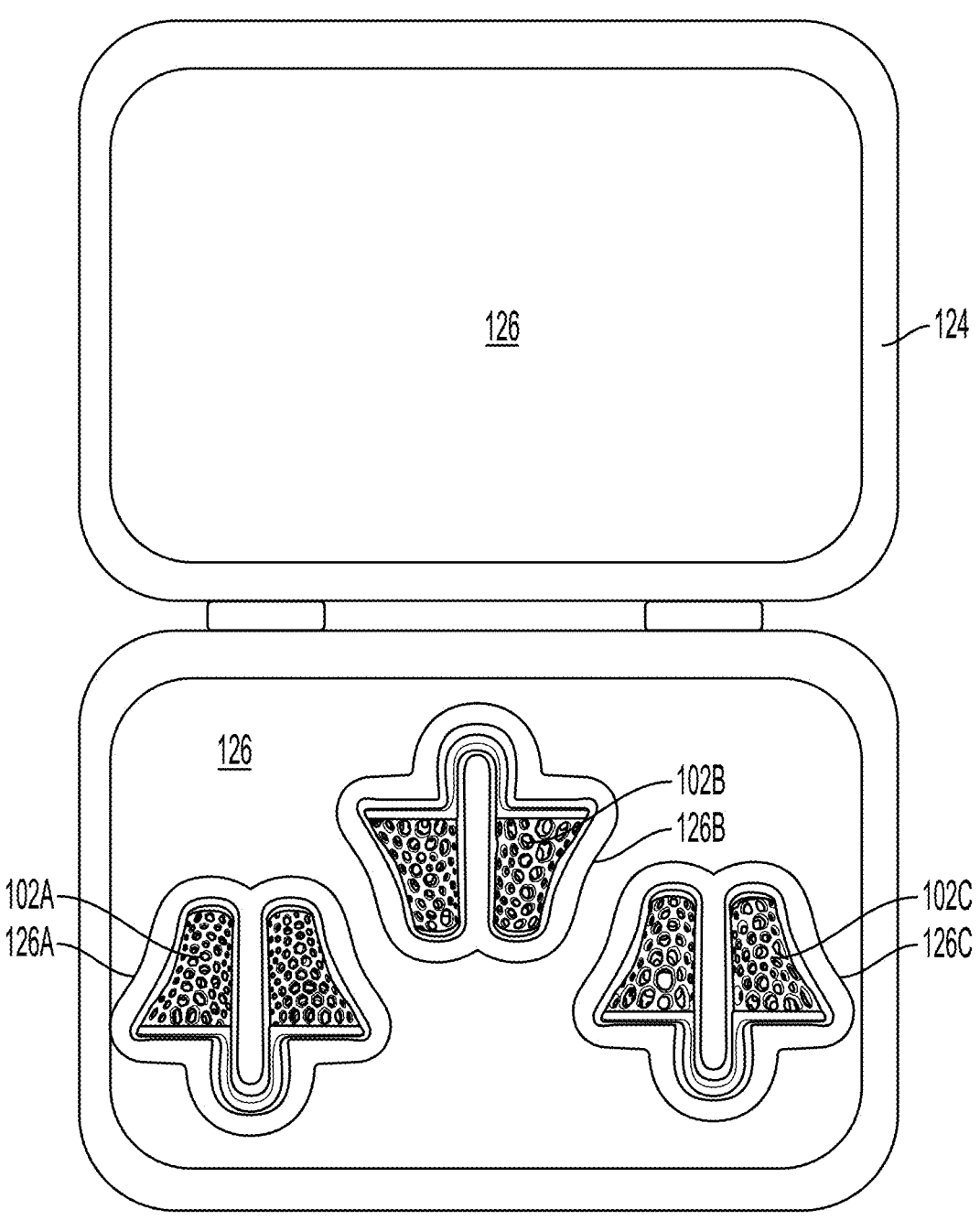
FIG. 7 depicts a storage case for storing the sets of nasal dilators of the system in accordance with embodiments of the present invention.

In some embodiments, the pattern of the plurality of interconnected struts 112 and openings 114 of the first nasal insert 104 of a set instance of the at least two sets of nasal dilators differ from a pattern of the plurality of interconnected struts and openings of the second nasal insert 106 of the set instance of the at least two sets of nasal dilators 102. Examples of this can be seen in FIG. 5 and FIG. 6. Here, each set of nasal dilators 102D, 102E, 102F makes use of different patterns of a first insert 104 and second insert 106 from a different set of the nasal dilator 102A, 102B, 102C provided previously. Thus, the fourth dilator set 102D makes use of a first insert 104B from the second dilator set 102B and a second insert 106A from the first dilator set 102A. The fifth dilator set 102E makes use of a first insert 104C from the third dilator set 102C and a second insert 106B from the second dilator set 102B. The sixth dilator set 102F makes use of a first insert 104A from the first dilator set 102A and a second insert 106C from the third dilator set 102C. FIG. 6 shows the dilator sets 102D, 102E, 102F of FIG. 5 using the color coding of FIG. 4.

In certain embodiments, the system 100 further comprises a storage case 124 sized, dimensioned, and configured for storing the at least two sets 102 of nasal dilators when not in use. An example of this can be seen in FIG. 7. Here the storage case 124 is a clamshell design with interior cavity 126 to hold the sets of dilators 102A, 102B, 102C, in their individual cavities 126A, 126B, 126C, though other configurations known to those of skill in the art are considered to fall within the scope of the present invention. The storage case 124 individual cavities 126A, 126B, 126C optionally may include identifiers formed of symbols, colors, and/or shapes, such as to identify the individual set of dilators contained therein e.g., by a day of the week or other information.

In certain embodiments where a connector 108 is utilized to connect the first nasal insert 104 to the second nasal insert 106, the connector 108 is sized, shaped, and configured to apply a force on the first 104 and second 106 inserts pushing the first 104 and second 106 inserts together. In other embodiments, the connector 108 is sized, shaped, and configured to apply a force on the first 104 and second 106 inserts pushing the first 104 and second 106 inserts apart.

In certain embodiments, the at least two sets of nasal dilators 102 are disposable after a single use. In other embodiments, the at least two sets of nasal dilators 102 are reusable and can be cleaned and/or sterilized for repeated use.

Figure 8:
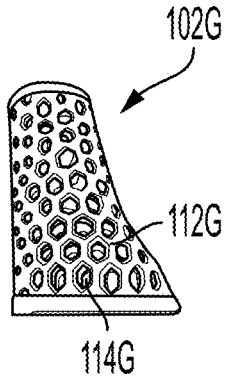
FIG. 8. is an example of a nasal dilator system where the sets of nasal dilators comprise a single nasal insert.
Figure 8:
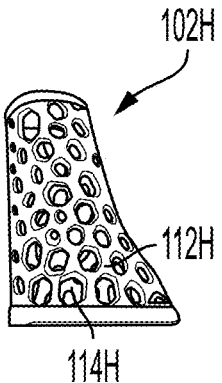
Figure 8:
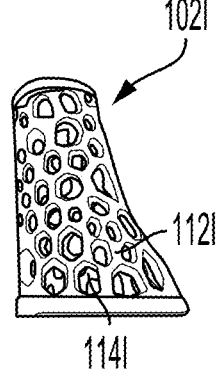

While the examples set forth above in FIGS. 2-7 involve each set of nasal dilators 102 having a first nasal insert 104 and a second nasal insert 106, it should be understood that a set could include only one nasal insert and, so long as there are at least two sets having different mesh patterns, can still provide the disclosed benefits. FIG. 8 depicts such an embodiment, where sets 102G, 102H, and 102I each include only one insert, but the mesh wall 110 of each insert has a different pattern of struts 112G, 112H, 112I and openings 114G, 114H, 114I.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may exist in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extent or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A nasal dilation system comprising at least two sets of nasal dilators, each set comprising:
a first nasal insert; and
a second nasal insert;
the first and second nasal inserts each having a mesh wall comprised of a plurality of interconnected struts and openings, the mesh wall forming a cannula extending between a base opening and a top opening;
wherein the first and second nasal inserts are sized, dimensioned, and configured in such a way as to be insertable to engage an outer surface of the mesh wall with an inner surface of nasal passages of a user, using a different insert of the set of inserts for each nasal passage; and
wherein a pattern of the plurality of interconnected struts and openings of a first set of the at least two sets of nasal dilators differs from a pattern of the plurality of interconnected struts and openings of a second set of the at least two sets of nasal dilators and cycling between the first set and the second set results in different impact patterns of the mesh walls upon the inner surface of nasal passages of a user thereby reducing repeated impact of a same inner surface portion across multiple sets of nasal dilators.

2. The nasal dilation system of claim 1, wherein the at least two sets of nasal dilators comprise three sets of nasal dilators.

3. The nasal dilation system of claim 1, wherein the at least two sets of nasal dilators comprise seven sets of nasal dilators.

4. The nasal dilation system of claim 1, wherein a pattern of the plurality of interconnected struts and openings of the first nasal insert of a set instance of the at least two sets of nasal dilators differs from a pattern of the plurality of interconnected struts and openings of the second nasal insert of the set instance of the at least two sets of nasal dilators.

5. The nasal dilation system of claim 1, where a cross-sectional area of each of the first and second inserts is substantially circular, ellipsoid, or rounded shape.

6. The nasal dilation system of claim 1, wherein a base opening cross-sectional area is greater than a top opening cross-sectional area.

7. The nasal dilation system of claim 1, wherein a cross-sectional area of each of the first and second inserts varies along a length of the cannula.

8. The nasal dilation system of claim 1, where the plurality of interconnected struts form irregular shaped openings therebetween.

9. The nasal dilation system of claim 1, wherein the plurality of interconnected struts and openings forms a non-uniform pattern.

10. The nasal dilation system of claim 1, where the at least two sets of nasal dilators are formed of a pliant material.

11. The nasal dilation system of claim 10, where the at least two sets of nasal dilators are formed of one or more of metal, plastic, polymer, and rubber.

12. The nasal dilation system of claim 1, wherein the first and second nasal inserts are comprised of a biocompatible material.

13. The nasal dilation system of claim 1, wherein the top opening is sized, dimensioned, and configured to maintain the first and second nasal inserts in place within the nasal passages via a friction fit.

14. The nasal dilation system of claim 1, wherein the base opening is sized, dimensioned, and configured to maintain the first and second nasal inserts in place within the nasal passages via a friction fit.

15. The nasal dilation system of claim 1, wherein varying effects produced by the first and second nasal inserts upon an internal lining of nasal passages of the user comprises increased airflow through the nasal passages.

16. The nasal dilation system of claim 1, wherein the at least two sets of nasal dilators further comprise identifiers to distinguish each set from another.

17. The nasal dilation system of claim 16, wherein the identifiers comprise one or more of symbols, colors, and shapes.

18. The nasal dilation system of claim 1, further comprising a storage case sized, dimensioned, and configured for storing the at least two sets of nasal dilators when not in use, the storage case optionally comprising identifiers formed of symbols, colors, and/or shapes.

19. The nasal dilation system of claim 1, wherein the at least two sets of nasal dilators are disposable after a single use.

20. The nasal dilation system of claim 1, wherein the at least two sets of nasal dilators are reusable and can be cleaned or sterilized for repeated use.

21. The nasal dilation system of claim 1, wherein the at least two sets of nasal dilators are provided in a variety of shapes to accommodate different shapes of nasal passages.

22. The nasal dilation system of claim 1, further comprising a connector connecting the first inserts to the second insert proximal the base openings of each insert.

23. The nasal dilation system of claim 22, wherein the connector is sized, shaped, and configured to apply a force on the first and second inserts pushing the first and second inserts together.

24. The nasal dilation system of claim 22, wherein the connector is sized, shaped, and configured to apply a force on the first and second inserts pushing the first and second inserts apart.

25. The nasal dilation system of claim 1, wherein the pattern of the plurality of interconnected struts and openings is generated via a randomizing process such as to be unique, at least across a very large number of variants.

26. A nasal dilation system comprising at least two sets of nasal dilators, each set comprising:

a nasal insert having a mesh wall comprised of a plurality of interconnected struts and openings, the mesh wall forming a cannula extending between a base opening and a top opening and wherein the nasal insert is sized, dimensioned, and configured in such a way as to be insertable to engage an outer surface of the mesh wall with an inner surface of nasal passages of a user; and wherein a pattern of the plurality of interconnected struts and openings of a first set of the at least two sets of nasal dilators differs from a pattern of the plurality of interconnected struts and openings of a second set of the at least two sets of nasal dilators and cycling between the first set and the second set results in different impact patterns of the mesh walls upon the inner surface of nasal passages of a user thereby reducing repeated impact of a same inner surface portion across multiple sets of nasal dilators.

\* \* \* \* \*